US00PP37639P2

(12) United States Plant Patent
van Hilst

(10) Patent No.: US PP37,639 P2
(45) Date of Patent: Aug. 18, 2026

(54) ***LEWISIA* PLANT NAMED 'MARIANNE'**

(50) Latin Name: *Lewisia cotyledon*
Varietal Denomination: MARIANNE

(71) Applicant: Philip van Hilst, Kaatsheuvel (NL)

(72) Inventor: Philip van Hilst, Kaatsheuvel (NL)

( * ) Notice: Subject to any disclaimer, the term of this patent is extended or adjusted under 35 U.S.C. 154(b) by 0 days.

(21) Appl. No.: 19/301,485

(22) Filed: Aug. 15, 2025

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 5/02; A01H 5/00; A01H 6/00
See application file for complete search history.

(56) References Cited

PUBLICATIONS

All Plant Young Plants Tissue Culture Catalogue 2026 retrieved on Nov. 13, 2025 at https://digitaalpubliceren.com/allplant/21022/88/#zoom=true, one cover page, one introductory page, pp. 1 and 86. (Year: 2025).*

IPM Essen 2025 IPM Essen 2025 Records Significant Increase in Vistors, retrieved on Nov. 12, 2025 at https://www.ipm-essen.de/press/press-texts/detail/ipm-essen-2025-records-significant-increase-in-visitors-6456, 3 pp. (Year: 2025).*

Plantipp 2025 Not just three, but five awards for Plantipp at IPM Essen 2025, retrieved on Nov. 12, 2025 at https://plantipp.eu/de/news/not-just-three-but-five-awards-for-plantipp-at-ipm-essen-2025, 3 pp. (Year: 2025).*

Plantipp 2025A Lewisia cotyledon Sunset Glow ('Marianne' PBR) EU 20250310, retrieved on Nov. 12, 2025 at https://plantipp.eu/uk/varieties/lewisia-cotyledon-sunset-glow-mariannepbr, 2 pp. (Year: 2025).*

* cited by examiner

*Primary Examiner* — June Hwu

(57) ABSTRACT

A new and distinct cultivar of *Lewisia* plant named 'Marianne' is disclosed, characterized by intense red star-shaped flowers blooming in late spring to early summer, with a second flush from September to frost. Plants are compact and densely-flowering, forming a beautiful mound. The new cultivar is a *Lewisia*, typically produced as an outdoor ornamental plant.

2 Drawing Sheets

Latin name of the genus and species: *Lewisia cotyledon.*
Cultivar denomination: 'MARIANNE'.

BACKGROUND OF THE INVENTION

The new cultivar *Lewisia* 'MARIANNE' is a chance discovery by the inventor at a nursery in Hoogkarspel, The Netherlands. The parents are unknown. The discovery of the new cultivar was made during 2021 as a chance seedling among a planting of unnamed *Lewisia cotyledon* plants.

Asexual reproduction of the new cultivar 'MARIANNE' was first performed in Hoogkarspel, The Netherlands during 2021 by tissue culture. This and subsequent propagation has shown that the unique features of this cultivar are stable and reproduced true to type in successive generations.

SUMMARY OF THE INVENTION

The cultivar 'MARIANNE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MARIANNE' These characteristics in combination distinguish 'MARIANNE' as a new and distinct *Lewisia* cultivar:

1. Intense red flower color that can be pinkish-red with yellow in warmer weather, and more intense red in colder weather.
2. Eye-catching star-shaped flowers in late spring to early summer with a second flush from September to frost.
3. First flowers appear already after 6 weeks after planting plugs.
4. Compact and densely flowering. Flowers form a beautiful mound.

PARENT COMPARISONS

Plants of the new cultivar 'MARIANNE' could not be compared with the parent cultivars, as they are unknown.

COMMERCIAL COMPARISONS

Plants of the new cultivar can be compared to plants of the *Lewisia* cultivar 'Elise Ruby Red', unpatented. Plants of the new *Lewisia* differed from plants of the cultivar 'Elise Ruby Red' in the following characteristics:

1. Flower color of the new cultivar is red, while the flower color of this comparator is pink.

Plants of the new cultivar can be compared to plants of the *Lewisia* cultivar 'Safira Coral', unpatented. Plants of the new *Lewisia* differed from plants of the cultivar 'Safira Coral' in the following characteristics:

1. Flower color of the new cultivar is red, while the flower color of this comparator is pink.

BRIEF DESCRIPTION OF THE PHOTOGRAPHS

Figure 1:
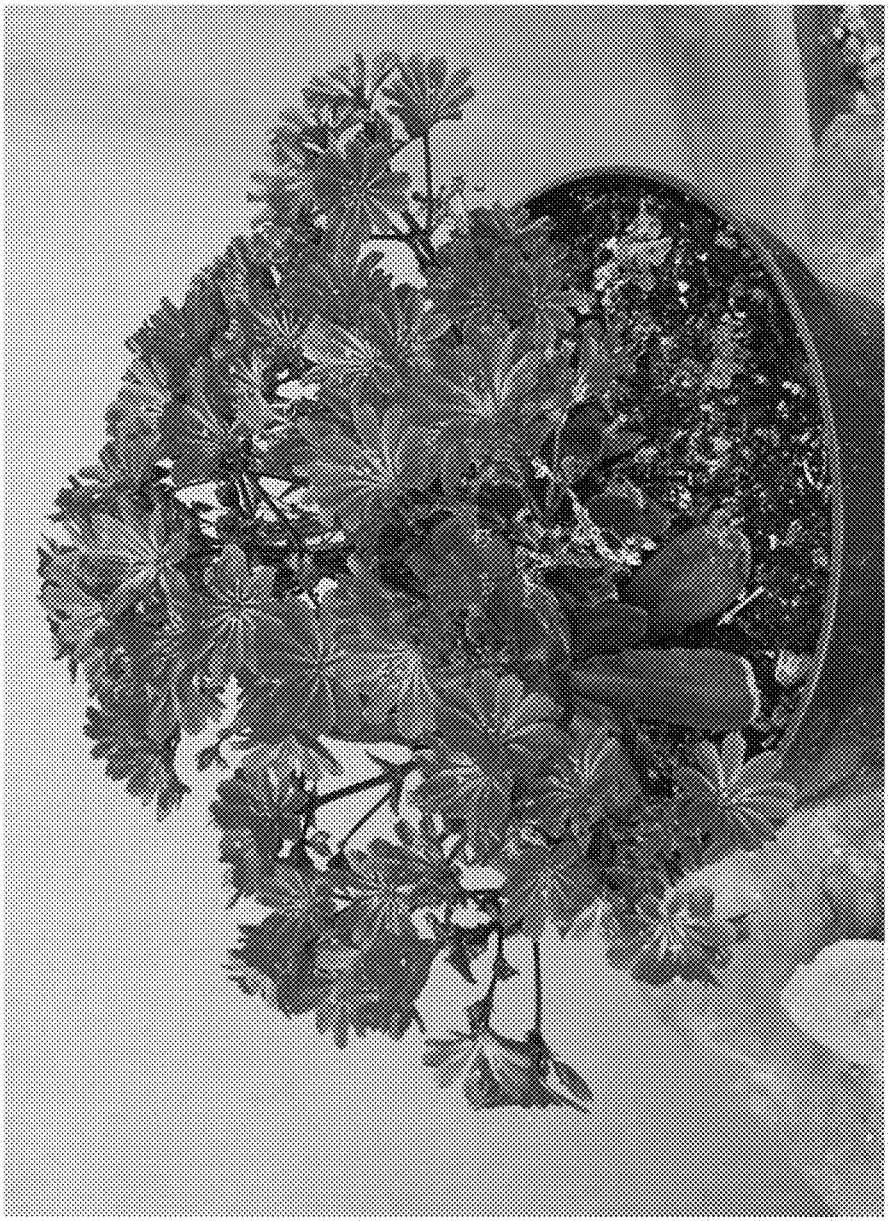

The accompanying photograph in FIG. 1 illustrates in full color a typical plant of 'MARIANNE' grown in de Lier, the Netherlands. This plant was about 9 months old, grown with 1-cutting in the pot. Photographs were taken in June. During the production of the plants, day temperatures ranged from about 5° to 15° C. and night temperatures ranged from 2° to 12° C.

Figure 2:
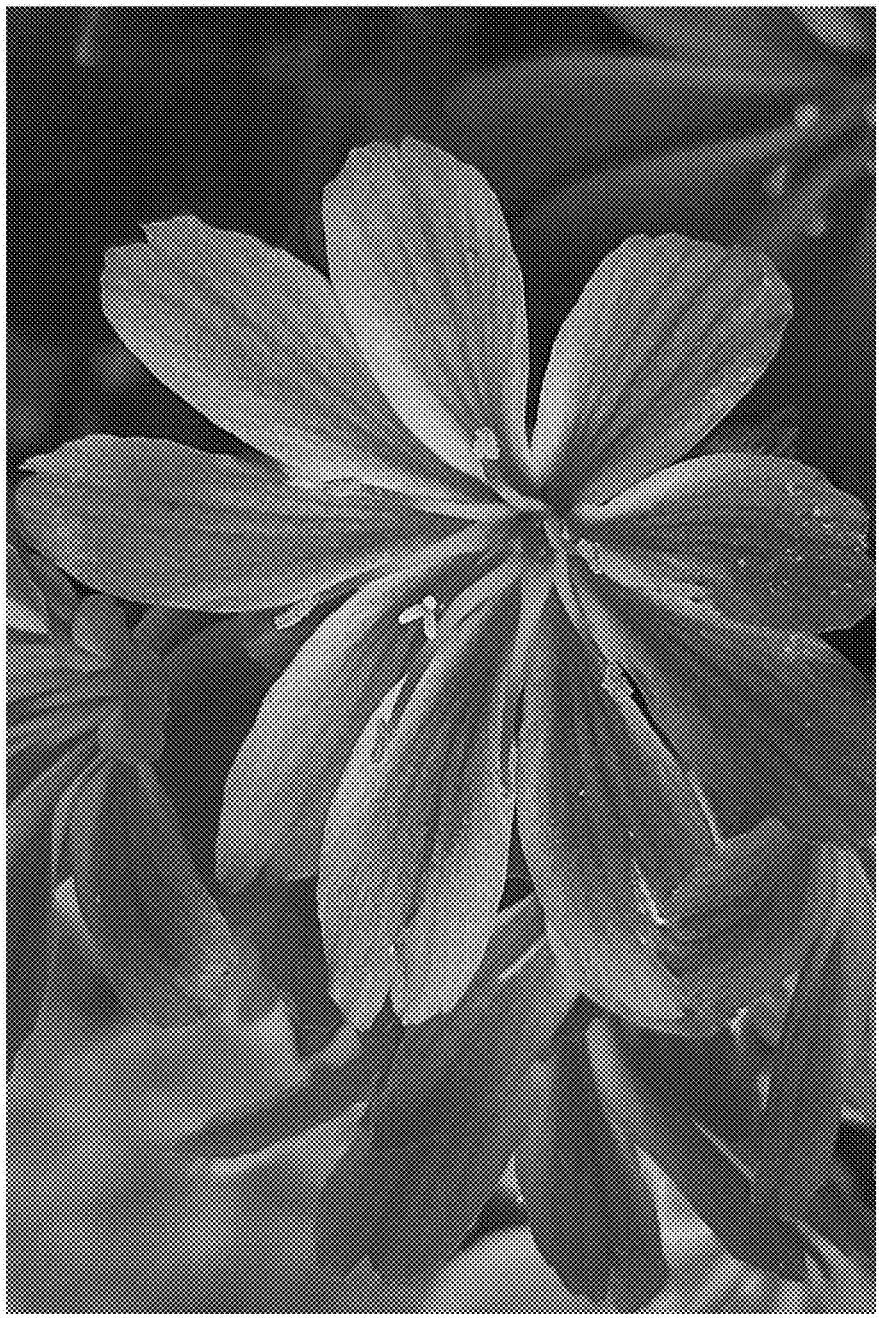

FIG. 2 illustrates a close-up of a typical flower of 'MARIANNE' in July.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'MARIANNE' plants grown indoors in de Lier, the Netherlands. During the production of the plants, day temperatures ranged from about 1.5° C. to 25° C. and night temperatures ranged from 1.5° C. to 15° C. No chemical or photoperiodic treatments were given. Measurements were taken during Spring and numerical values represent averages of typical flowering types.

Botanical classification: *Lewisia cotyledon* 'MARIANNE'.

PROPAGATION

Method: Tissue culture.
Time to produce a rooted plant: About 6 weeks.
Root description: Fine, brown.

PLANT

Plant form/habit: : Herbaceous evergreen perennial.
Height: 14 cm to floral plane; 5.5 cm to foliar plane.
Plant spread: 19 cm.
Branching characteristics: Basal rosette.

FOLIAGE

Leaf:
- *Division*.—Simple.
- *Length*.—8 cm.
- *Width*.—1.3 cm.
- *Shape*.—Narrowly oblanceolate.
- *Apex*.—Apiculate to acute.
- *Base*.—Narrowly cuneate.
- *Margin*.—Entire.
- *Texture of top surface*.—Glabrous.
- *Texture of bottom surface*.—Glabrous.
- *Color*.—Developing foliage upper side: RHS Green 137B with Yellow-Green 144B at base. Developing foliage under side: RHS Yellow-Green 144A with 145B and 145C streaks. Mature foliage upper side: RHS Green 137A, midrib Yellow-Green 144A. Mature foliage under side: RHS Yellow-Green 144A, midrib and base 145B and 145C.
- *Venation*.—Pinnate. Vein color is indistinguishable from the leaf blade.

FLOWER

Bloom period: April to May. Another flowering occurs September to frost.

Inflorescence:
- *Type*.—Panicle.
- *Height*.—5 cm, excluding peduncle.
- *Diameter*.—6 cm.

Persistence: Persistent.
Fragrance: Very light somewhat clove-like.
Flowers per Inflorescence: 18 to 24.

Flower bud:
- *Length*.—0.9 cm.
- *Diameter*.—0.4 cm.
- *Shape*.—Oblong.
- *Color*.—RHS Red 45A.
- *Texture and appearance*.—Glabrous and slightly glossy.

Individual flower:
- *Shape*.—Rotate.
- *Diameter*.—2.5 cm.
- *Depth*.—1.5 cm.

Petals:
- *Quantity*.—9.
- *Length*.—1.5 cm.
- *Width*.—0.6 cm.
- *Shape*.—Oblanceolate.
- *Apex*.—Emarginate.
- *Base*.—Cuneate.
- *Margin*.—Undulate.
- *Texture and appearance, upper and lower surfaces*.—Glabrous, slightly glossy on upper side.
- *Color*.—Mature petals, upper surface: RHS Red N45B to N45C, along lower margins Orange-Yellow 21A. Light veins Red N45A. Mature petals, lower surface: RHS Red 45B to 45C, veins 45A, Orange-Yellow 21A at lower margins. Fading petals, upper surface: RHS Red 53C to 53D, veins 53B to 53C. Fading petals, lower surface: RHS Red 53C to 53D, veins 53B to 53C.

Floral bract:
- *Size*.—About 8 mm long and 3 mm wide.
- *Shape*.—Lanceolate.
- *Apex*.—Acute.
- *Texture*.—Smooth all surfaces.
- *Color, upper and lower surfaces*.—Yellow-Green 144B flushed 144A.

Sepals:
- *Quantity*.—2.
- *Length*.—0.4 cm.
- *Width*.—0.4 cm.
- *Shape*.—Broadly ovate.
- *Apex*.—Obtuse.
- *Base*.—Obtuse.
- *Margin*.—Glandular/gland-toothed.
- *Texture upper surface*.—Glabrous.
- *Texture lower surface*.—Glabrous.
- *Color*.—RHS Yellow-Green 144C to 144D, veins 144A.

Calyx:
- *Depth*.—0.4 cm.
- *Diameter*.—0.4 cm.

Peduncle:
*Length.*—6 cm.
*Diameter.*—0.3 cm.
*Aspect.*—30° from vertical.
*Strength.*—Moderate.
*Color.*—Young: RHS Yellow-Green 144B. Mature: RHS Yellow-Green 144A with faded layer of Reddish-Orange 175B.
*Texture.*—Glabrous.
Pedicel:
*Length.*—0.3 cm.
*Diameter.*—1 mm.
*Texture.*—Glabrous.
*Strength.*—Moderate.
*Color.*—RHS Yellow-Green 144B.

REPRODUCTIVE ORGANS

Gynoecium:
*Pistil number.*—1.
*Pistil length.*—0.7 cm.
*Stigma shape.*—Cleft.
*Stigma diameter.*—0.05 cm.
*Stigma length.*—0.05 cm.
*Stigma color.*—RHS Yellow 8C.
*Style length.*—0.5 cm.
*Style diameter.*—0.1 cm.
*Style color.*—RHS Purple-Red 63A.
*Ovary color.*—RHS Purple-Red 63A.
Androcoecium:
*Stamen number.*—7.
*Filament color.*—RHS White N155C with Purple-Red 63A to 63B.
*Filament length.*—0.9 cm.
*Anther shape.*—Oblong.
*Anther length.*—0.1 cm.
*Anther diameter.*—0.05 cm.
*Anther color.*—RHS Reddish-Orange 169A.
*Amount of pollen.*—Moderate.
*Pollen color.*—RHS Yellow 16A.

OTHER CHARACTERISTICS

Disease resistance: Plants of the new *Lewisia* have not been noted to be resistant nor susceptible to pathogens and pests common to *Lewisia*.
Temperature tolerance: Plants of the new *Lewisia* have been observed to be winter hardy to about −15° C.
Fruit/seed production: Not observed.

What is claimed is:

1. A new and distinct cultivar of *Lewisia* plant named 'Marianne' as herein illustrated and described.

* * * * *